US00PP08056P

United States Patent [19]

Zampini

[11] Patent Number: Plant 8,056

[45] Date of Patent: Dec. 8, 1992

[54] DWARF FLOWERING CRAB APPLE TREE NAMED LANZAM

[75] Inventor: James W. Zampini, 5052 S. Ridge Rd., Perry, Ohio 44081-0122

[73] Assignee: James W. Zampini, Perry, Ohio

[21] Appl. No.: 631,250

[22] Filed: Dec. 20, 1990

[51] Int. Cl.[5] ..... A01H 5/00

[52] U.S. Cl. ..... Plt./35.2

[58] Field of Search ..... Plt./34

[56] References Cited

PUBLICATIONS den Boer, A. F., "Chapter Six, Flowers, Color–Types–Form", *Ornamental Crab Apples,* American Association of Nurserymen, Jul. 1959, pp. 35–37.

*Primary Examiner*—James R. Feyrer

*Attorney, Agent, or Firm*—Burns, Doane, Swecker & Mathis

[57] ABSTRACT

A new and distinct variety of dwarf flowering crab apple tree named Lanzam is provided. The new variety can be readily distinguished from the Toringo crab apple tree (nonpatented in the United States). For instance, the new variety forms attractive dark red buds which open into white blossoms, has a compact and twiggy growth habit, has ovate-elliptic leaves, and consistently produces distinctive golden-colored fruit. The new variety is particularly well suited for growing as attractive ornamentation in the landscape.

4 Drawing Sheets

SUMMARY OF THE INVENTION

The new and distinct variety Malus crab apple tree was discovered during 1976 as a seedling of unknown parentage while growing in a cultivated area tended by man. More specifically, the new variety was discovered while growing among trees of the Toringo crab apple (*Malus sieboldii*) being grown on the Kohankie Farm located at Perry, Ohio in Zone 6a. The seed parent of the new variety is believed to be *Malus sieboldii* and the pollen parent is unknown.

My attention was initially attracted to a single plant of the new variety since it was found to exhibit a combination of characteristics which differ significantly from those of the Toringo crab apple tree. Had I not discovered and preserved this new tree it would have been lost to mankind.

It has been found that the new and distinct flowering crab apple tree of the present invention exhibits the following combination of characteristics:

(a) exhibits a dwarf compact, upright, broadly conical and twiggy growth habit,
(b) forms a profusion of attractive dark red buds which open into white blossoms,
(c) consistently forms attractive golden-colored fruit, and
(d) forms ovate-elliptic leaves as opposed to *Malus sieboldii* which commonly forms three-lobed leaves.

Trees of the new variety have been asexually reproduced by budding onto *Malus domestica* understocks. Propagation by softwood cuttings has proven to be 95 percent successful. The characteristics of the new variety have been found to be strictly transmissible by such asexual propagation from one generation to another.

The new variety has been named the Lanzam variety. Also, trees of the new variety are being marketed under the Lancelot trademark.

BRIEF DESCRIPTION OF THE PHOTOGRAPHS

The accompanying photographs show as nearly true as it is reasonably possible to make the same in color illustrations of this character, typical specimens of the tree and plant parts of the new variety. The specimens depicted were grown at Perry, Ohio.

Figure 1:
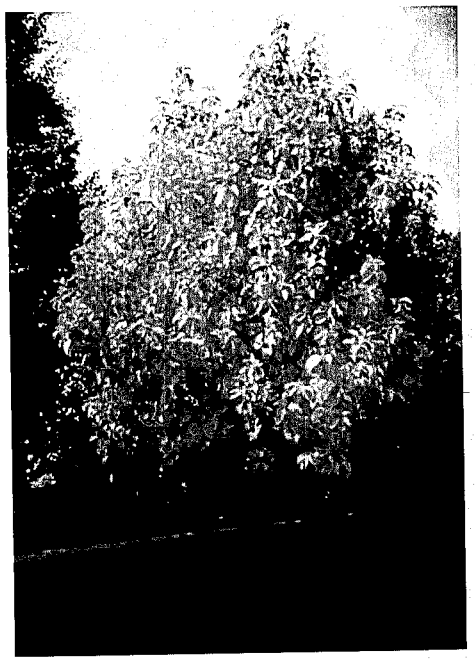
FIG. 1 illustrates a fourteen year-old tree of the new variety during autumn while the leaves are undergoing their usual seasonal color transformation from green to gold.
Figure 2:
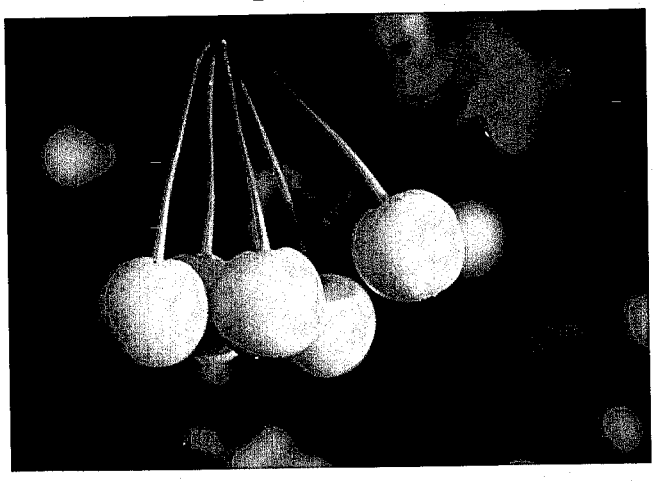
FIG. 2 illustrates representative specimens of the attractive golden fruit of the new variety while present on the tree.
Figure 3:
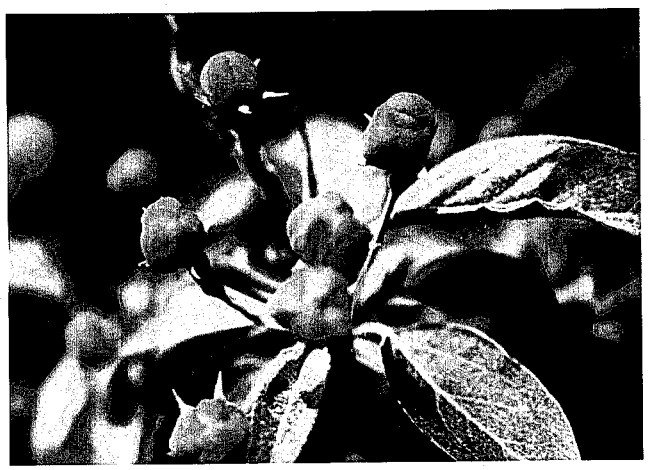
FIG. 3 illustrates a close-up view of several flower buds, as well as some representative somewhat immature leaves.
Figure 4:
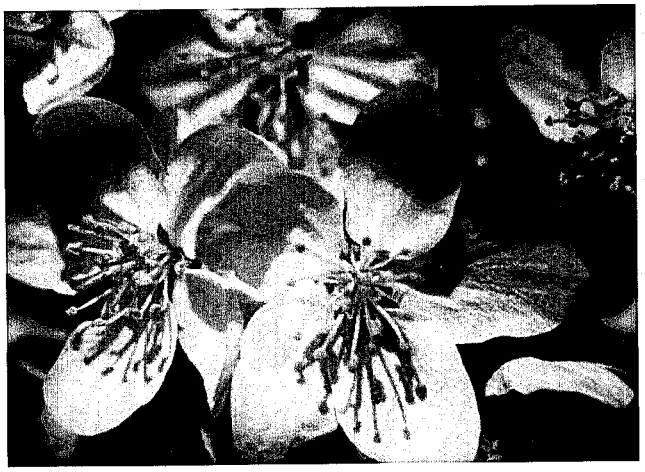
FIG. 4 illustrates a close-up view of several blossoms.
Figure 5:
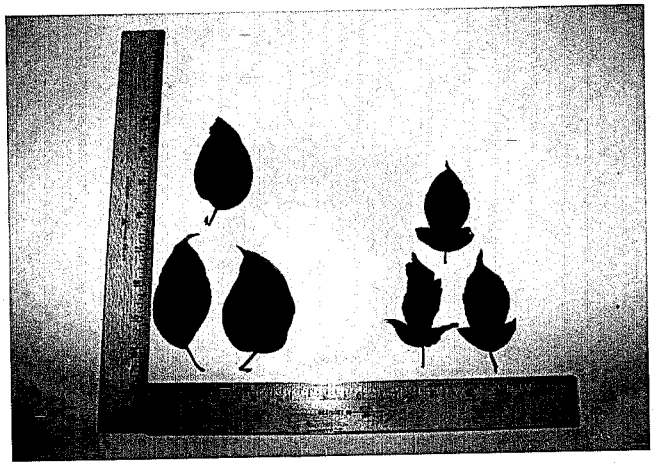

FIG. 5 illustrates for comparative purposes representative ovate-elliptic leaves of the new variety on the left and representative three-lobed leaves of the Toringo crab apple tree on the right. The photograph was made during early November thus the color variations are attributable to the fall environment. The disparity in leaf shape and size is apparent.

Figure 6:
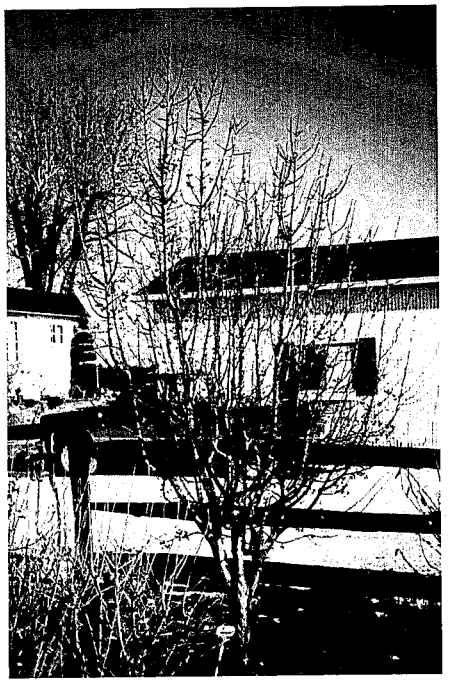

FIG. 6 illustrates the upright and twiggy growth habit of the new variety.

DETAILED DESCRIPTION

The chart used in the identification of colors is that of the Royal Horticultural Society (R.H.S. Colour Chart). Other references to color are to be accorded their ordinary dictionary significance. The descriptions are based upon trees grown at Perry, Ohio.

The original tree of the new variety exhibits a genetically controlled dwarf growth habit and is approximately 8½ feet tall, approximately 5 feet wide, and has a caliper of approximately 5 inches at grade. Accordingly, the new variety exhibits a compact, upright, broadly conical and twiggy growth habit. When grown on its own roots, the tree is expected to reach a height of approximately 10 feet and a width of approximately 8 feet at full maturity. On the contrary the Toringo apple tree commonly assumes a height of 10 to 15 feet and sometimes reaches a height of 30 feet in the wild.

Also, the Toringo apple tree commonly is a wide, if not wider, than it is tall.

The new variety exhibits a considerably more upright growth habit than the Toringo apple tree wherein the branches leave the tree in a somewhat horizontal configuration and are arching or pendulous. While the new variety could be considered to form a central leader, such leader is not dominant due to the overall growth habit. The new variety is estimated to be approximately four times more dense than the Toringo apple tree.

For a genetically dwarf tree, the new variety is considered to be very vigorous. When the new variety is compared to the Toringo crab apple at Perry, Ohio, trees of the same age are found to exhibit substantially the same caliper. However, in all instances the trees of the Toringo apple are taller and wider than the new variety. Since the distance between internodes along the branches is much shorter on the new variety, many more scaffold branches are exhibited.

The blossom appearance of the new variety can be readily distinguished from that of the Toringo crab apple tree which is known to produce pink buds which open into pink flowers which fade to white. On the contrary, the present variety forms in profusion attractive dark red buds which open into pure white blossoms. The dark red coloration of the buds generally corresponds to that of Red Group 53B, and when the blossoms are open, the blossom coloration has have been found commonly to correspond to that of White Group 155D. No blossom fragrance has been observed to date.

The leaves commonly are approximately three-fourths to completely open at the time of flowering.

The configuration of the flowers is generally typical of the genus, and in particular of that of the Toringo crab apple tree. The flowers of the new variety are perfect, single and extremely numerous. Blooming commonly occurs from mid-April to mid-May at Perry, Ohio, and commonly lasts approximately 10 to 14 days following its onset. Such flowers commonly are borne in 5 to 6 umbellate clusters on slender pedicels having a length of approximately $\frac{3}{4}$ inch which arise from fruiting spurs having a length of approximately $\frac{1}{2}$ inch. The flowers commonly average approximately 1 to $1\frac{1}{4}$ inch at the broadest point when fully expanded. The corolla consists of 5 broadly obovate petals which narrow abruptly to slender claws of approximately $\frac{1}{8}$ inch in length. The slender and acute calyx lobes are reflexed. The new variety produces pollen which is believed to be self fertile.

Except for the shape of the leaves, the vegetative and reproductive parts of the variety are in most respects typical of the genus, and in particular of that of the Toringo crab apple tree. The leaves are usually alternate, simple ovate-elliptic and serrulate. The leaf coloration during mid-season commonly approximates that of Yellow-Green Group 146B on the upper surface and tends to be paler on the under surface. The leaves have a generally rounded base and commonly end in an acuminate tip. The leaves are pubescent on both sides. The leaves of vegetative shoots commonly reach a length of approximately 3 to $3\frac{3}{4}$ inches and include a petiole commonly measuring approximately $\frac{3}{4}$ inch in length. The leaves of fruiting shoots tend to be smaller in size and variable in all dimensions. The fruiting spurs average approximately $\frac{1}{2}$ inch in length. The immature twigs are maroon and villous with small orange lenticels which persist with age. Winter buds are medium chocolate brown in coloration and generally are glabrous except for some densely white villous margins of the bud scales. The fall leaf coloration approximates Yellow-Orange Group 22A.

The fruit of the new variety undergoes the usual color changes. The immature fruit of the new variety initially is bright green, changes to yellow, and subsequently develops a bright golden-yellow coloration (as illustrated) which commonly approximates Yellow-Orange Group 15C when ripe. The fruit stem coloration when supporting the ripe fruit commonly approximates Red Group 44B. It will eventually turn a deep golden coloration before it assumes a brownish coloration when overripe by late January when it begins to fall from the tree. The fruit is a small globose pome containing two single-seeded locules. Such fruit averages approximately $\frac{3}{8}$ to $\frac{1}{2}$ inch in diameter. Upon maturity, the fruit acquires a faint waxy bloom and the calyx is abscising. The fruit is formed in a substantially uniform manner each year. Accordingly, the new variety cannot be considered to be an alternate bearing tree.

When grown at Perry, Ohio, the new variety has exhibited disease resistance and has not been affected to any degree by diseases and insects which are common to crab apple trees. Additionally, the new variety has been shown to be highly resistant to scab when tested in Pennsylvania and Wisconsin. The new variety has proven to be hardy when grown in Zone 4. For example, on Jan. 21, 1985, it was exposed to a low temperature of $-18°$ F. without a deleterious impact. Also, considerable drought resistance has been exhibited by the new variety. For instance, the average annual precipitation at Perry, Ohio is understood to be 35.4 inches. In two out of the last four years the area has experienced severe drought conditions. In 1988 the annual precipitation was only 29.69 inches and in 1991 the annual precipitation was only 32.67 inches. The new variety withstood these conditions without any known damage.

I claim:

1. A new and distinct variety of flowering crab apple tree which exhibits the following combination of characteristics:

(a) exhibits a dwarf, compact, upright, broadly conical and twiggy growth habit,
(b) forms a profusion of attractive dark red buds which open into white blossoms,
(c) consistently forms attractive golden-colored fruit, and
(d) forms ovate-elliptic leaves as opposed to *Malus sieboldii* which commonly forms three-lobed leaves;

substantially as herein shown and described.

* * * * *